(12) United States Patent
Hartwick

(10) Patent No.: US 6,578,751 B2
(45) Date of Patent: Jun. 17, 2003

(54) METHOD OF SEQUENTIALLY FIRING STAPLES USING SPRINGS AND A ROTARY OR LINEAR SHUTTER

(75) Inventor: Darrell J. Hartwick, Brighton, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/962,684

(22) Filed: Sep. 26, 2001

(65) Prior Publication Data

US 2003/0057251 A1 Mar. 27, 2003

(51) Int. Cl.[7] .............................................. A61B 17/068
(52) U.S. Cl. .................... 227/176.1; 227/19; 227/180.1; 606/219
(58) Field of Search ........................ 227/175.1, 176.1, 227/180.1, 19; 606/219

(56) References Cited

U.S. PATENT DOCUMENTS

| | | | |
|---|---|---|---|
| 4,881,544 A | * 11/1989 | Green et al. .................. 227/19 |
| 5,395,030 A | 3/1995 | Kuramoto et al. |
| 5,667,517 A | * 9/1997 | Hooven .................... 227/176.1 |
| 5,728,119 A | * 3/1998 | Smith et al. ................. 606/190 |
| 6,119,913 A | 9/2000 | Adams et al. |
| 6,126,058 A | * 10/2000 | Adams et al. ............ 227/180.1 |
| 6,149,660 A | * 11/2000 | Laufer et al. ............. 227/175.1 |
| 6,179,195 B1 | * 1/2001 | Adams et al. ............ 227/180.1 |
| 6,241,140 B1 | 6/2001 | Adams et al. |
| 6,279,809 B1 | 8/2001 | Nicolo |
| 6,315,184 B1 | 11/2001 | Whitman |
| 2001/0002029 A1 | 5/2001 | Geiste et al. |

* cited by examiner

*Primary Examiner*—Scott A. Smith
(74) *Attorney, Agent, or Firm*—Kenyon & Kenyon

(57) ABSTRACT

A minimally invasive medical stapling device comprises a housing that contains spring-loaded staples for use in a minimally invasive medical stapling procedure. When the physician pulls a shutter the springs are sequentially released causing the staples to be fired. The device provides the user with tactile and audible feedback as the staples are fired.

21 Claims, 7 Drawing Sheets

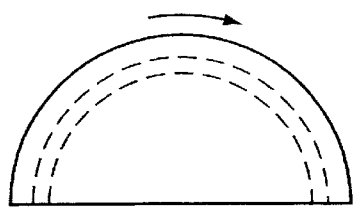
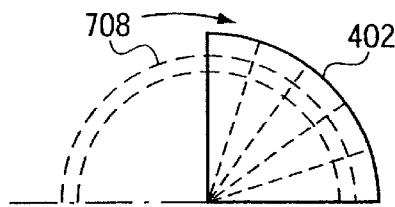
*Fig. 6A*        *Fig. 6B*
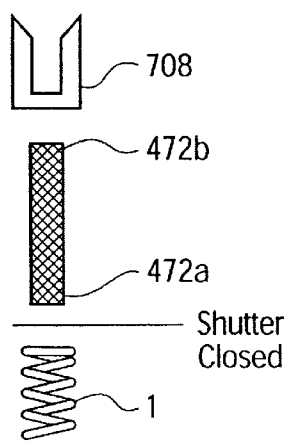
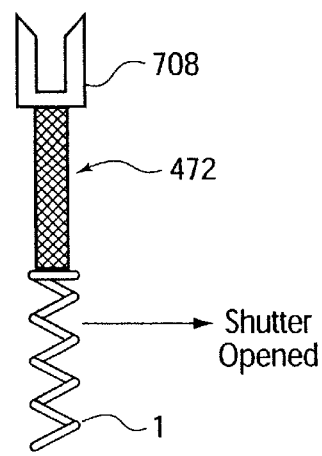
*Fig. 7A*        *Fig. 7B*

METHOD OF SEQUENTIALLY FIRING STAPLES USING SPRINGS AND A ROTARY OR LINEAR SHUTTER

FIELD OF THE INVENTION

The present invention relates to medical fastening devices and methods for use in minimally invasive surgery.

BACKGROUND INFORMATION

Minimally invasive surgery has been used in many formerly complex medical procedures, such as gall bladder removal, urological and reproductive operations, valve repair and replacement and by-pass operations. Minimally invasive surgery involves inserting tools into a patient through a natural opening or small incision in the body. The surgical tools are then manipulated from outside the patient. This approach to surgery has a number of advantages, including, inter alia, that it is generally less traumatic, smaller incisions, if any, are needed, and the patient has less post-operative pain and a shorter recovery time.

Minimally invasive surgery requires tools that a surgeon can trust. In particular, a surgeon needs reliable indication of when and how a procedure is completed. Ideally, tactile, audible and visual confirmation of operation is available to surgeons.

A resectioning procedure will be used in this disclosure as a specific example of a technique requiring a fastening device, such as the present invention, and a procedure suitable for minimally invasive surgery. There is no intention to limit the present disclosure to resectioning or endoscopic surgery in particular. The fastening device could, for example, be used in laproscopic surgical procedures. A resectioning procedure involves excising a portion of an organ, fastening the surrounding tissue together to close up the hole created by the excision, and removing the excess tissue. Various conventional devices and procedures are available for resectioning lesions in tubular organs.

A Full Thickness Resectioning Device (FTRD) comprises a fixed housing, a removable cartridge body containing staples, a large diameter rotary shaft slidable within the removable cartridge body, the staple drivers having a staple end adjacent to the staples and a driven end and an actuator disposed in the fixed housing, the actuator moving the staple drivers to push the staples against an anvil portion of the FTRD when in the attached configuration. The standard fastening device used in the FTRD has more custom-machined parts than the present invention, increasing its cost. Additionally, the rotary shaft used to control the fastener is relatively stiff, preventing free passage of the FTRD, particularly past the pelvic brim.

The terms "fastener," "suture" and "staple" are used in this disclosure as understood by persons skilled in the art. Those skilled in the art will understand that "sutures" and "staples" are examples of "fasteners" and that the term "fastener" may include other elements.

The term "proximal" refers to an element of the apparatus located closer to the outside of the patient's body or the user of the apparatus or device. "Distal" refers to an element or part of the device located farther inside the patient's body or from the user of the apparatus or device.

SUMMARY OF THE INVENTION

A method of firing fasteners by removing a wire or shutter from between springs and the fasteners, which sequentially releases each spring is disclosed.

A minimally invasive medical fastening device comprising spring loaded fasteners fired, or deployed, by sequentially releasing a shutter is also disclosed.

BRIEF DESCRIPTION OF THE DRAWINGS

FIGS. 6a and 6b show a rotary shutter that may be used in the present invention;

FIGS. 7a and 7b show a perspective cut-away view of the driving structure of the device of FIG. 1;

DETAILED DESCRIPTION

Figure 1:
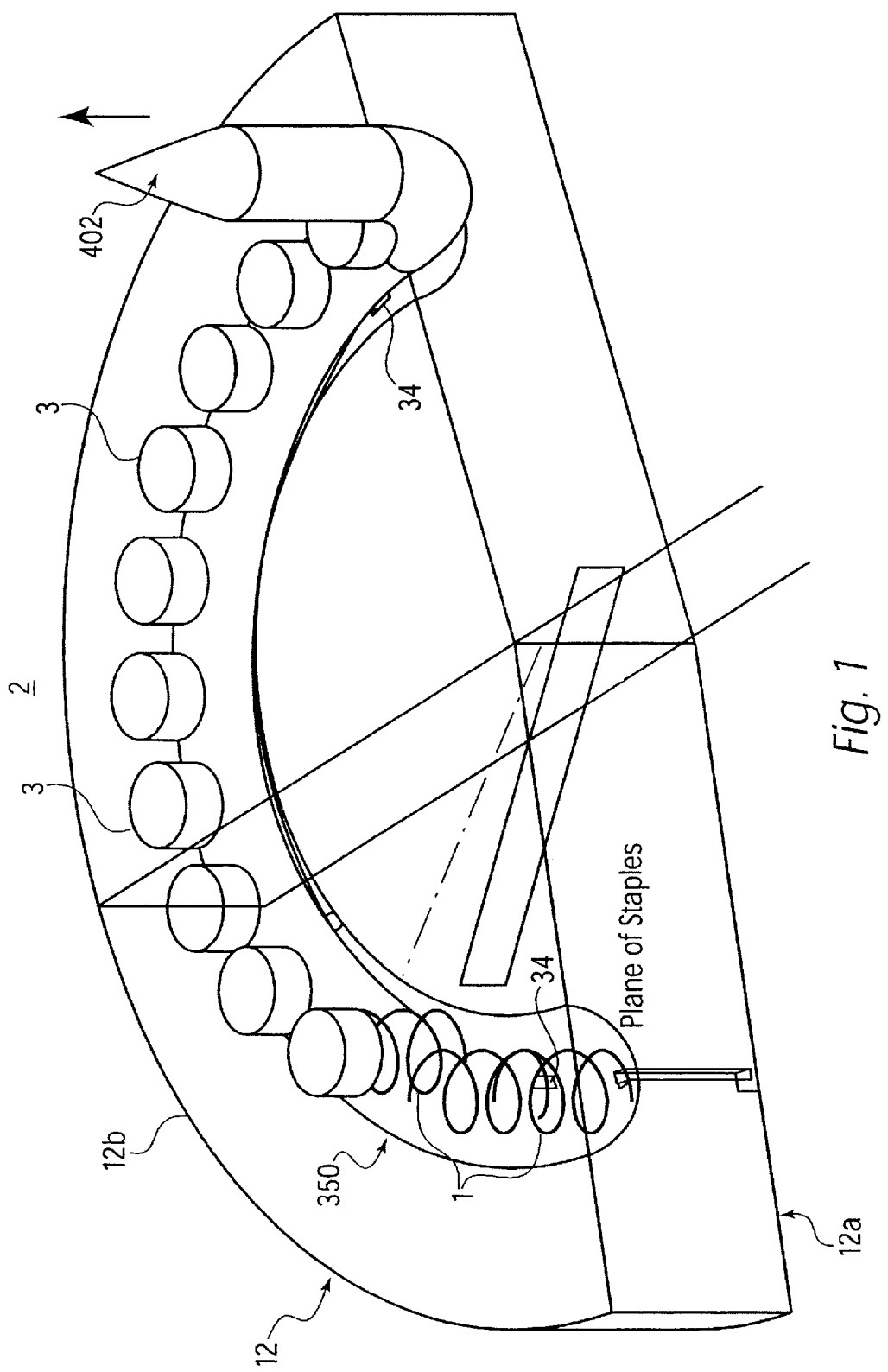
FIG. 1 shows a fastening device according to a first embodiment of the present invention.

As shown in FIGS. 1–5, an apparatus according to a first embodiment of the present invention comprises a fastening device 2 in which springs 1 are used to propel the fasteners 708, shown in FIG. 7, through the material to be fastened. The springs 1 may be packaged in a pre-compressed state beneath pistons 3, as shown in FIG. 1. The compression of each spring at the time of manufacture allows the force to be applied to each staple 708 to be accurately predetermined. The springs may be manufactured from any bio-compatible metal of suitable strength, preferably steel. Those skilled in the art will recognize that the springs may also be fitted into the housing 12 in pre-formed recesses or otherwise fixedly attached to the housing 12.

The springs 1 are separated from the staples 708 by a shutter 402. The shutter may be a linear shutter as shown in FIG. 1 or a rotary shutter as shown in FIGS. 6a and 6b. As the shutter 402 is pulled from between the springs 1 and the staples 708, the potential energy stored in the springs 1 upon compression is released as a driving force. Each spring moves from a compressed to a decompressed position in a discrete burst, impelling the staples 708 through the staple slits 34 against the staple-forming grooves 19 in the anvil 10, shown in FIG. 5. The shutter may be fabricated from metal or a plastic strong enough to retain the springs in their compressed state. A linear shutter or trip wire may be fabricated from a bio-compatible metal wire or cable, for example, that can be pulled from between each spring and staple pair in the direction of the arrow shown in FIG. 1 and wrapped around a drum in the control handle, similarly to fishing line in a fishing rod. A linear shutter may be used that is only as big as the minimum required active part of the shutter between the staples and the spring. This small linear shutter has the advantage of being physically smaller than other firing mechanisms known in the art. A rotary shutter on the other hand, would be wider, since it would have to be rotated from between the staples and the springs to an open position.

A rotary shutter would intervene between the springs 1 and the staples 708 and could be removed from therebetween by telescoping open in an iris-like manner, by rotating 180 degrees, or by folding open in an accordian-like manner, as shown in FIGS. 6a and 6b. An iris-type rotary shutter and an accordian-like rotary shutter both have the advantage that once the shutter has been released it is no longer blocking any other devices that may be used in the procedure, such as for example a blade or grasping device.

A plurality of staple slits 34 is preferably disposed in a substantially circular row extending along the periphery of the distal end 12a of the proximal housing 12. The staple slits 34 extend from one side of the proximal housing to the other. The plurality of staple slits 34 may preferably be arranged so that when the anvil member 10 is in the most proximal position, each of the staple slits 34 is aligned with a corresponding one of the staple-forming grooves 19.

When the device is configured for operation, a plurality of staples 708 is received within the fastening device 2. Each of the staples 708 is aligned with a respective one of the staple slits 34. The staples 708 are then sequentially fired from the respective staple slits 34 by springs 1 (shown in FIG. 1) disposed in the proximal housing 12 and released by a trip wire or shutter 402. The staples 708 may be fabricated from titanium or other bio-compatible fastening materials.

A track 350 is provided within the stapler head 12 extending over the row of staple slits 34. The track 350 may preferably be situated substantially proximal to the plurality of staple slits 34 on the staple face 12b. The linear shutter 402 may be situated so that it slides along the track 350 and is supported thereby, reducing the tensile strength required of the shutter itself.

Instead of dragging one cam or driver across the unformed staples 708 in order to gradually press them against the anvil as in the prior art, each staple is impelled against the anvil by its own spring and staple driver as each spring is released by the shutter. Furthermore the linear shutter or trip wire may be controlled by a wire having a substantially smaller diameter than the rotary shaft required by prior art fasteners. For example, the linear shutter or trip wire may be controlled by a wire having a diameter as narrow as about 1/16th of an inch or less, as compared to a diameter or about 1/4 inch in certain prior art devices. This smaller diameter allows the device to be more easily maneuvered within the patient.

Optionally, a staple driver 472, shown in FIG. 7, extends substantially longitudinally, proximally from each of the staple slits 34. Each staple driver 472 is slidably received within the fastening device 2 for motion between a pre-loaded, proximal position and a staple driving, distal position. In the pre-loaded position, an upper end of each of the staple drivers 472 is completely received within the proximal housing 12, just proximal of a respective staple.

The staple drivers 472 are preferably substantially rectangular in shape, although bottom edges 472a thereof may more preferably be rounded. The length of the staple drivers 472 is preferably selected so that, in the pre-loaded position, the springs 1 will fit into the proximal housing 12. The bottom surfaces 472a are, in the pre-loaded position, more preferably substantially aligned with the distal most projection of the shutter 402.

Thus in operation, the shutter 402 is opened so that the springs 1 successively drive each of the staple drivers 472 into contact with a corresponding staple so that each staple driver 472 and its staple are driven distally through a respective one of the staple slits 34. This drives the staples 708 across the gap from the distal end 12a into the anvil member 10, through any tissue held between the anvil member 10 and the proximal housing 12, and into the corresponding staple forming grooves 19. Thus the section of the tissue gripped between the anvil member 10 and the proximal housing 12 is stapled in a pattern substantially the same as that formed by the staple slits 34 (i.e., substantially circular).

In operation, the user applies a force to the control handle 6 to open the shutter 402. The shutter 402 releases the springs 1 sequentially so that they contact the staple drivers 472. The springs 1 then individually drive the staple drivers 472 distally as described above to staple the tissue received between the anvil member 10 and the proximal housing 12.

After an organ section has been stapled between the anvil member 10 and the proximal housing 12, a blade is drawn through the stapled tissue. Then the wall of the body passage is released and the lesion tissue remains within the gap between the distal end 12a and the anvil member 10 held by grasping devices. The lesion tissue may then be withdrawn from the body for analysis.

Those skilled in the art will understand that the anvil member 10 may have tapered shapes such as a bullet-like structure without departing from the scope of the present invention. The distal end 16 of the anvil member 10 may preferably have a beveled edge adjoining the first endoscope lumen 13 to allow for an expanded field of forward vision via the endoscope 8. The proximal housing 12 may preferably have a cross section corresponding in size and shape to the cross section of the proximal face 14 of the anvil member 10 (i.e., substantially circular or elliptical). However, those skilled in the art will understand that the cross-sectional shape of the grasper holes may be selected to, for example, accommodate another type of device.

Those skilled in the art will understand that many different types of fasteners may be used either alone or in combination for this purpose so long as the fasteners do not impede the steering of the endoscope 8 or the rotation of the cables. Those skilled in the art will understand that tape (e.g., surgical, electrical, etc.), electrical cable, rubber bands, other belt-style fasteners, etc. may be used as fasteners.

The fastening device 2 comprises an anvil member 10 coupled to a distal end 12a of a proximal housing 12. The anvil member 10 has a substantially crescent-shaped cross-section with a proximal face 14 and a smaller distal face 16. The cut-out 13 of the anvil member 10 is included to allow the endoscope 8 to be slid through the fastening device 2 so that the endoscope 8 may be advanced into the body passage allowing the fastening device 2 to later be advanced into the body to the lesion. In addition, the cut-out 13 also provides forward vision via the endoscope 8. Thus, any shape of the cut-out 13 may be selected which is large enough to accommodate the endoscope 8. A larger cut-out provides a larger field of vision.

The fastening device 2 may preferably be connected to a distal end of a sheath 4. The proximal end of the sheath 4 may preferably be connected to a control handle 6.

Figure 2:
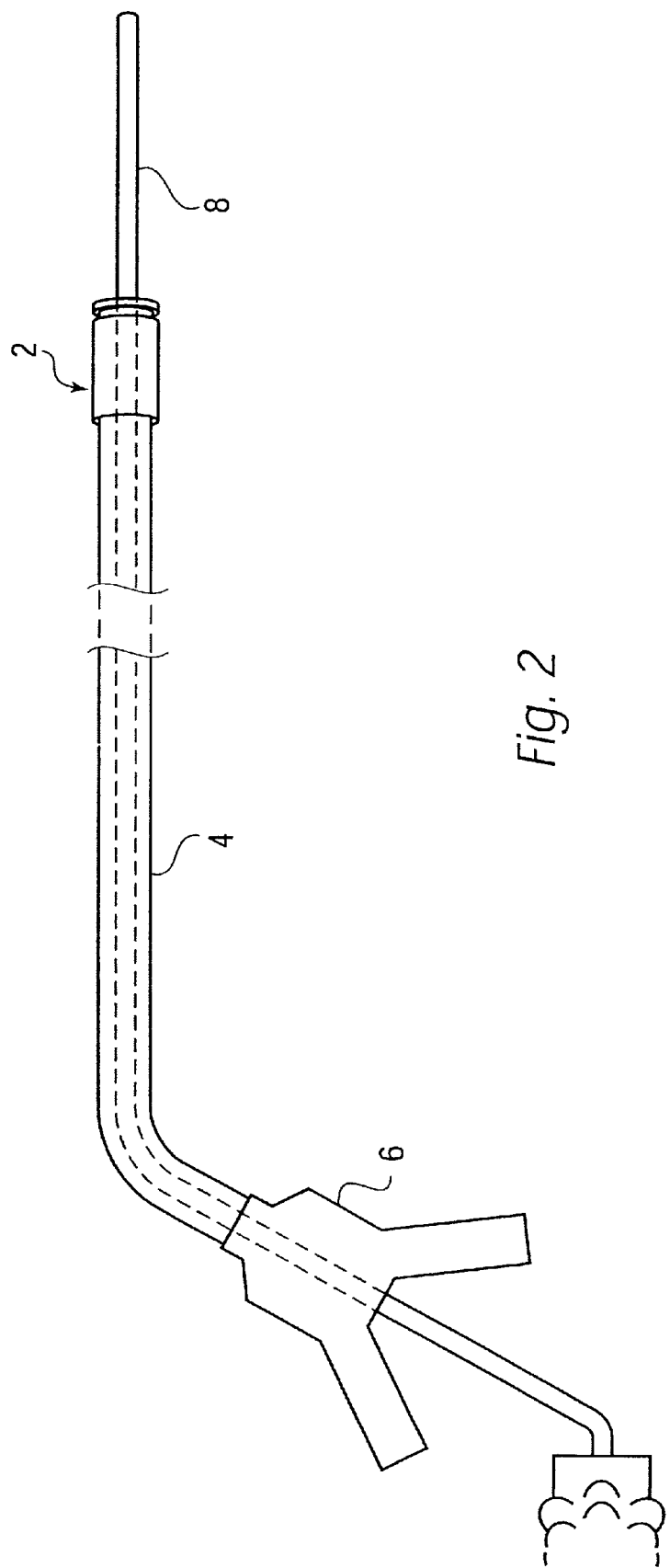
FIG. 2 shows the device of FIG. 1 mounted on a conventional endoscope.
Figure 3:
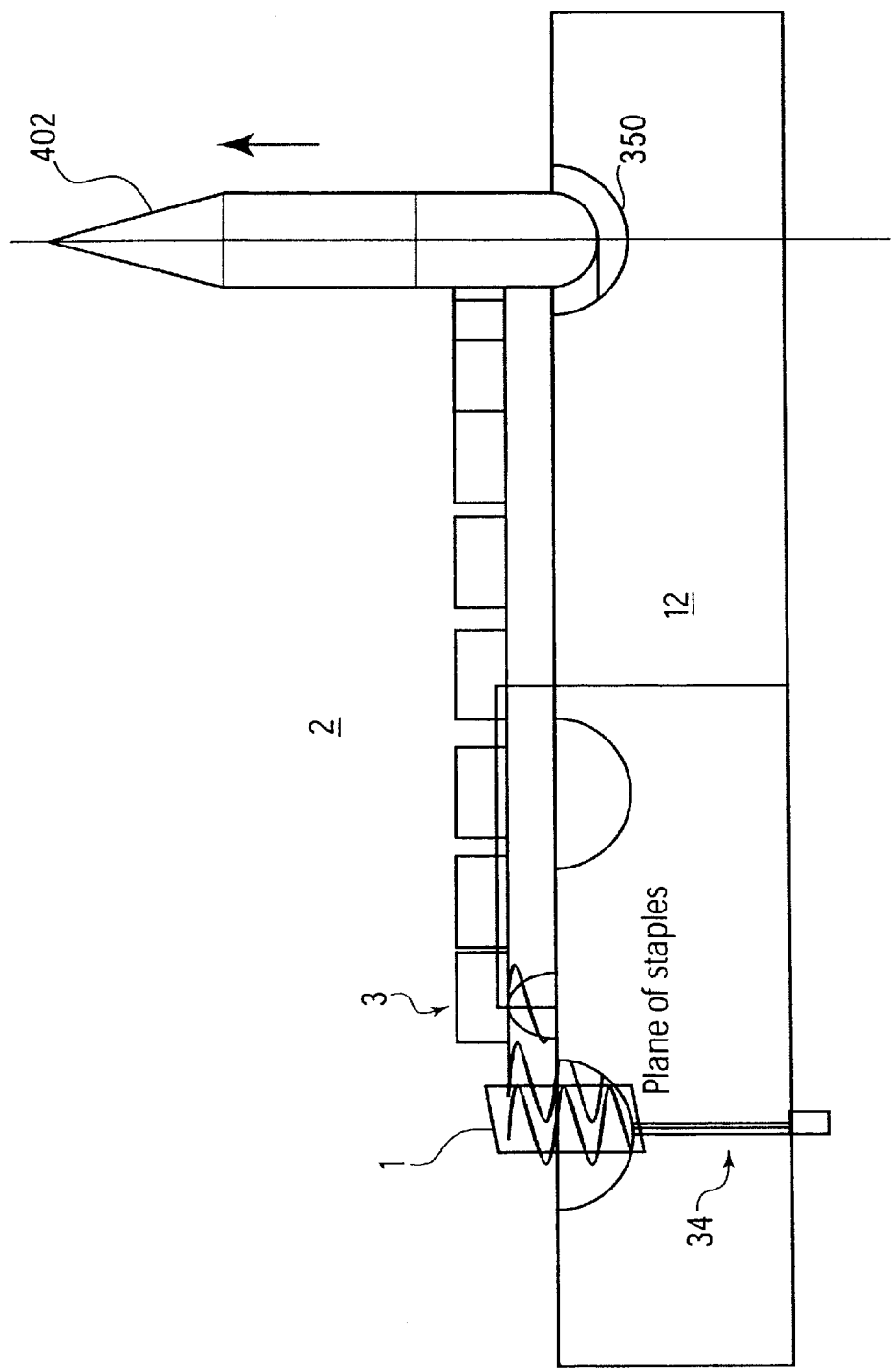
FIG. 3 shows a side view of the device of FIG. 1.
Figure 4:
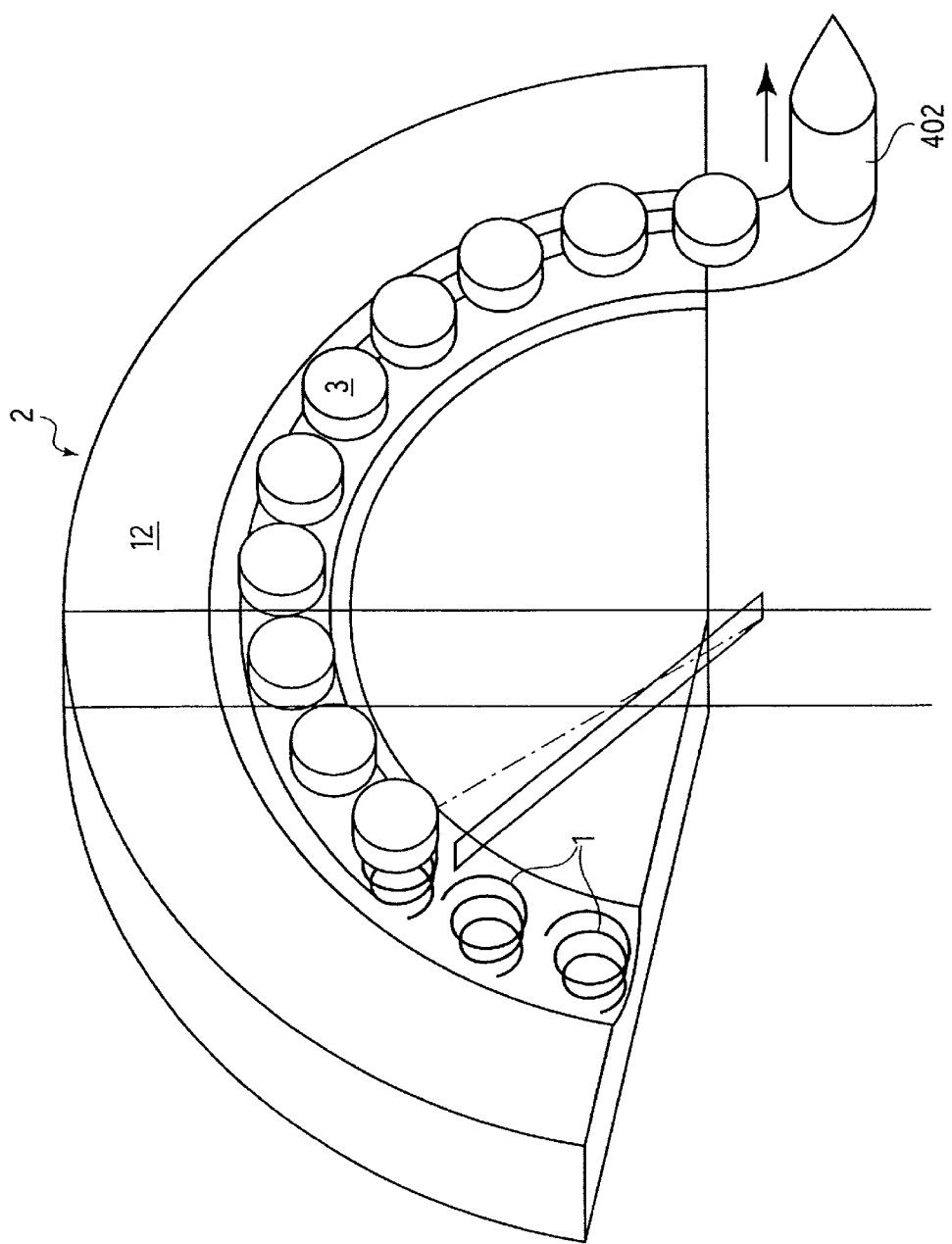
FIG. 4 shows a perspective of the device of FIG. 1 showing a spring loaded mechanism thereof.
Figure 5:
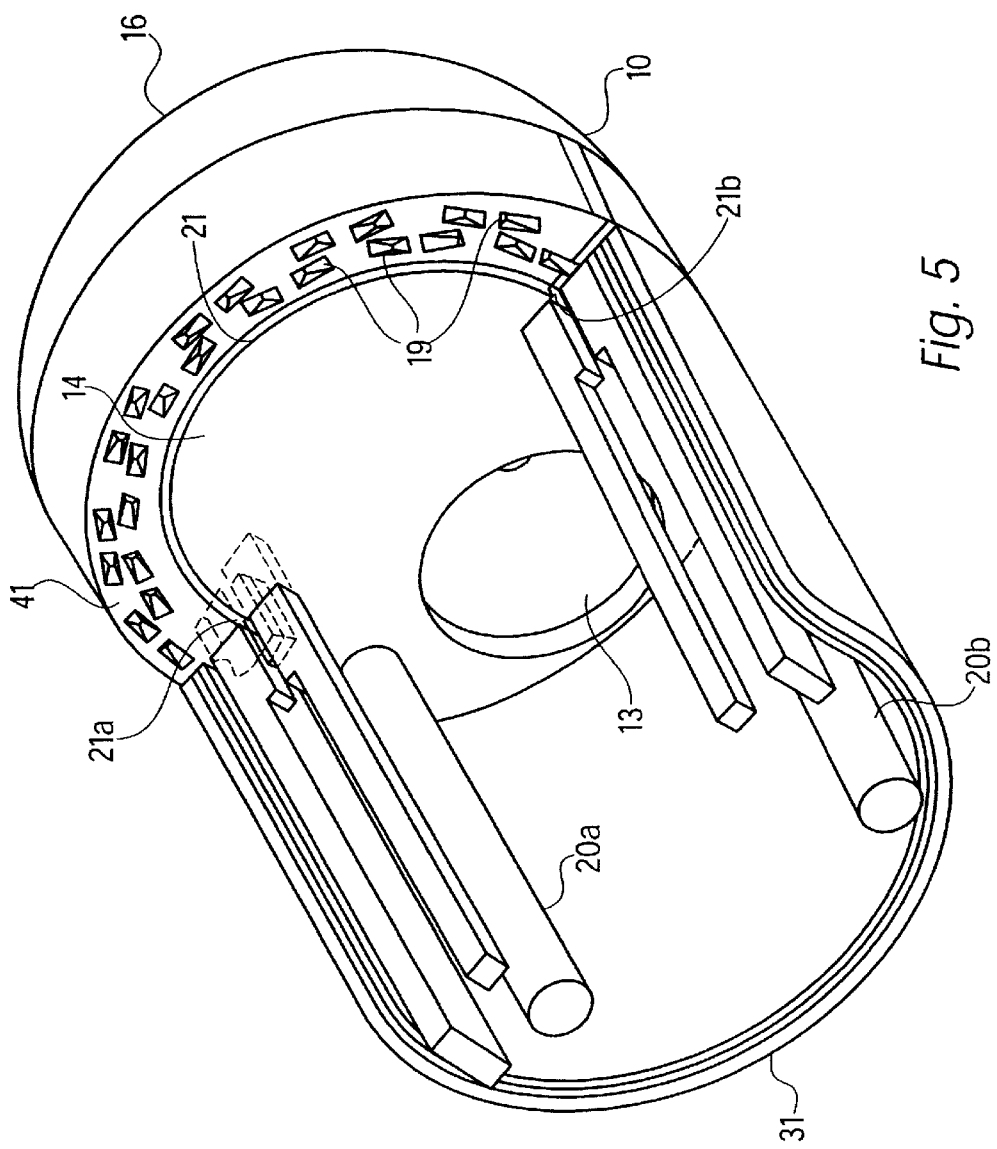
FIG. 5 shows a perspective of the device of FIG. 1 showing the anvil portion thereof.

In operation, the entire apparatus is mounted onto an endoscope 8 by passing the endoscope 8 through the control handle 6, the sheath 4, and the fastening device 2, as shown in FIG. 2. The endoscope 8 is then inserted into a body orifice to locate a lesion in the tubular organ under visual observation (usually while insufflating the organ). Once the lesion has been located, the fastening device 2 and the sheath 4 are slidably advanced along the endoscope 8 into the tubular organ until the fastening device 2 is in a desired position adjacent to the lesion.

The device may use a duodenoscope as the endoscope 8. Those skilled in the art will understand that other types of endoscopes may also be used, such as, for example, gastroscope, colonoscope, etc. Those skilled in the art will also understand that in an alternative embodiment, the fastening device 2 may also be detachably coupled to a distal end of the endoscope 8, and the entire arrangement may then be inserted into the body orifice under visual observation.

Although the anvil member 10 is shown fixedly coupled to the mounting shafts 20a, 20b, those skilled in the art will understand that the anvil member 10 may also be pivotally coupled to the mounting shafts 20a, 20b in order to provide a greater field of vision through the endoscope 8. The mounting shafts 20a, 20b are slidably received in mounting holes(not shown), which have a size and shape substantially corresponding to the size and shape of the mounting shafts 20a, 20b and which run axially through the proximal housing 12.

The mounting shafts 20a, 20b are preferably movable axially, proximally and distally within the mounting holes between a proximal most position in which a tissue gripping gap of a first predetermined width is formed between the rim 41 and the distal end 12a of the proximal housing 12, and a distal most position in which a tissue receiving gap of a larger second predetermined width is formed between the rim 41 and the distal end 12a of the proximal housing 12. The second predetermined width should preferably be more than twice the thickness of a wall of the organ being resectioned so that a section of the tubular organ may be pulled into a resectioning position between the anvil member 10 and the proximal housing 12.

Those skilled in the art will understand that the sheath 4 is preferably torsionally stiff to resist the torque forces from the drive cables rotating therein. However, the sheath 4 is longitudinally flexible to so that it may be slidably advanced along the endoscope 8, while minimizing interference with the operation of the endoscope 8 and trauma to surrounding tissue. The sheath 4 is preferably constructed similar to known endoscope insertion tubes, which are flexible yet allow the transfer of forces to swivel the distal end of the endoscope 8 in multiple directions and the torqueable rotation of the endoscope. The sheath 4 and the body of the patient act to muffle the feedback that may be heard or felt by the operating physician. The rapid decompression of each spring as each staple is fired may provide more audible feedback for the physician than with tradition stapling devices.

As shown in FIG. 1, at least the distal end 12a of the proximal housing 12 preferably has a cross-section corresponding in size and shape to the proximal face 14 of the anvil member 10, including a cutout (not shown) substantially corresponding in size and shape to the cutout 13 of anvil member 10. The cutout is provided to receive the endoscope 8 therein and allow the proximal housing 12 to be slidably advanced along the endoscope 8. Of course, those skilled in the art will understand that the shape of the outer surface of the fastening device 2 may be selected in order to accommodate various desired resectioning shapes, and the shape of the anvil member 10 may preferably be selected to form a continuous surface when positioned adjacent to the proximal housing 12 to facilitate advancing the fastening device to into, and removing it from, body passages. It is preferable for certain applications that the fastening device have a maximum diameter at any point between 15 mm and 40 mm.

A substantially circular blade slit (not shown) extends substantially radially within the staple slits 34 so that, when the anvil is in the proximal most position, the blade slit is aligned with the guiding slit 21 on the anvil member. When positioned at one end of the blade slit, a cutting blade is preferably completely enclosed within the respective one of the blade housing devices and the guiding slit 21, so that the cutting blade does not cut any tissue until the physician intentionally operates the blade. When the physician operates the blade, the blade is driven from its initial position around the blade slit with its cutting edge facing a direction of movement, following the path of the staples. Thus, after a cutting operation has been performed, the blade is once again prevented from inadvertently injuring the patient.

Figure 8:
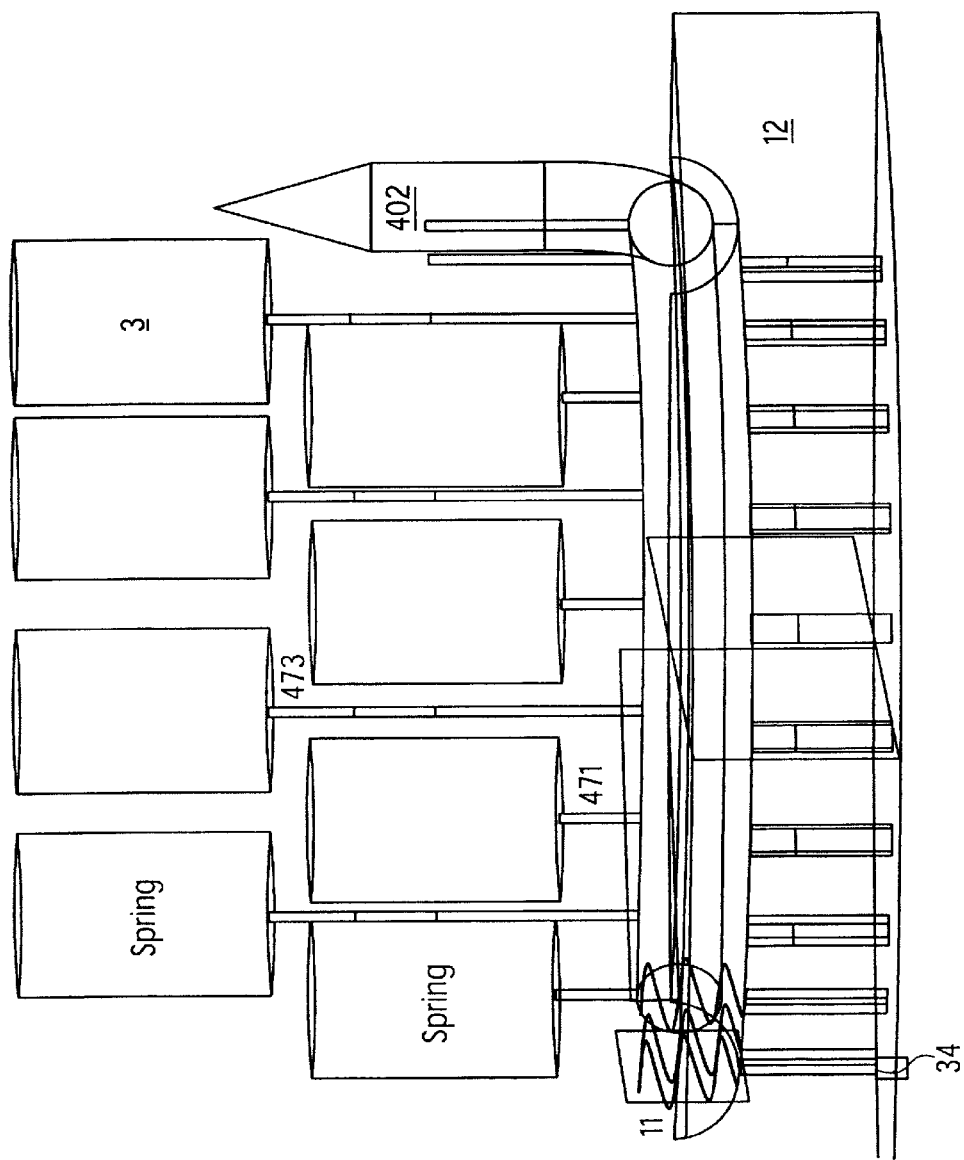
FIG. 8 shows another embodiment of the invention.

FIG. 8 shows a device according to a second embodiment of the present invention in which like reference numerals identify the same elements. In this embodiment, the length of the staple drivers is alternated between long 473 and short 471, allowing springs 11 of greater size to be used to propel the staples 708. In this case the long staple drivers are longer than the length of the compressed springs. The greater size of the spring in turn can store more potential energy with compression, allowing the staples 708 to be propelled with greater force. Additionally this embodiment would allow more fasteners to be used to secure the same length of tissue, since the limit of how closely the staples 708 could be packed would be determined only by the size of the staples 708, rather than the size of the springs. One skilled in the art will recognize that the length of the staple drivers may be varied in any way that will allow springs with the desired impelling force to be used. For example, staple drivers of three or more different lengths may be used alternately.

Those skilled in the art will understand that although the proximal housing 12 in any of the embodiments may preferably be composed of a metallic-type material, the proximal housing 12 may also be composed of a clear plastic-type material which would allow the user to operate the fastening device 2 under visual observation by partially withdrawing the endoscope 8 into the second endoscope lumen in the proximal housing 12. The user could then look through the walls of the endoscope lumen into the proximal housing 12 to, for example, observe whether each of the plurality of staple drivers 472 has been actuated. Alternatively, selected portions of the proximal housing 12 may be composed of the clear plastic-type material providing a "window" to view through the proximal housing 12.

Those skilled in the art will also understand that although the above-described embodiments show mechanical force transmission between the control handle and the working head assembly, this device could alternatively include an electronic control for receiving input from an operator coupled to a series of motors in the working head assembly. Those skilled in the art will further understand that the relative positioning of the stapling mechanisms and the position adjusting mechanisms to each other may be reversed, placing the stapling mechanisms in a distal-most position in relation to the position adjusting mechanism.

In a different embodiment, the fastening device according to the invention includes a removable portion that contains the staples 708 used by the firing mechanism. The removable portion is preferably mounted complementary to the proximal housing of the device, and can be removed and replaced by the operator to reload staples 708 during a procedure.

Staples 708 are held in staple containing cavities of the removable cartridge body. Staple drivers 472 are slidably disposed in guides 34 that are preferably formed in the removable cartridge body. When the removable cartridge body is in the attached configuration with the fixed housing, movement of the staple drivers 472 towards anvil member 10 causes staples 708 to be ejected through staple slits 34 from staple containing cavities, and be pushed against staple forming grooves 19. Staple drivers 472 have a staple end 472b that pushes on staple, and a driven end 472a, that is acted upon by a spring.

As described above, in a preferred embodiment successive adjacent staple drivers 472 are actuated sequentially, so that staples 708 are ejected starting from one end and finishing at the opposite end of the row of staple slits 34.

It will be apparent to one of ordinary skill in the art that different specific mechanisms can perform the desired functions according to the invention. In particular, it will be apparent that the stapler described can be placed either in the fixed housing or in the removable cartridge body.

As each spring is released and each staple is fired, the physician receives audible feedback in the form of a click. The physician can count the number of staples 708 fired to determine when the stapling process is complete. The completion of the stapling process signals that the stapling operation is complete, and the cutting operation is about to start.

The above described embodiments are for purposes of illustration only and the various modifications of these embodiments which will be apparent are considered to be within the scope of the teachings of this invention which is to be limited only by the claims appended hereto.

What is claimed is:

1. A minimally invasive medical fastening device comprising:
    a housing;
    a plurality of springs disposed in the housing;
    a plurality of staples;
    a shutter disposed in the housing between the plurality of springs and the plurality of staples; and
    an anvil member;
    wherein the shutter is movable sequentially from a first position in which the shutter holds all of the plurality of springs in a compressed condition, to a second position in which the movement of the shutter releases a first spring of said plurality of springs, causing a first staple of said plurality of staples to deploy, to an nth position in which the movement of the shutter has released all of the plurality of springs, causing all of said plurality of staples to deploy.

2. The minimally invasive medical fastening device according to claim 1, further comprising a plurality of staple drivers movably disposed in the housing, the staple drivers being disposed between the shutter and the plurality of staples.

3. The minimally invasive medical fastening device according to claim 2, wherein the staple drivers sequentially abut the staples when the shutter is removed from therebetween.

4. The minimally invasive medical fastening device according to claim 1, wherein the shutter is hand-operated from a proximal end of the minimally invasive medical fastening device.

5. The minimally invasive medical fastening device according to claim 1, wherein the shutter is a linear shutter.

6. The minimally invasive medical fastening device according to claim 1, wherein the shutter is a collapsible rotary shutter.

7. The minimally invasive medical fastening device according to claim 1, further comprising friction fittings to hold the springs before said springs are released by the shutter.

8. The minimally invasive medical fastening device according to claim 1, wherein the shutter is a trip wire.

9. A method of arranging and firing fasteners comprising the steps of:
    arranging a plurality of fasteners,
    arranging a plurality of compressed springs, each of said springs proximate to one of said fasteners;
    arranging a shutter between the springs and the fasteners; and
    sequentially releasing each spring and thereby deploying each fastener by removing the shutter.

10. A method according to claim 9 wherein said shutter is a linear shutter.

11. A method according to claim 9 wherein said shutter is a collapsible rotary shutter.

12. A method according to claim 9 wherein said shutter is a trip wire.

13. A minimally invasive medical fastening device comprising
    a housing,
    a plurality of fasteners contained in the housing,
    a plurality of springs,
    an anvil member,
    a shutter disposed between the springs and the fasteners, and
    a plurality of staple drivers disposed between the shutter and each spring.

14. The minimally invasive medical fastening device of claim 13, wherein the plurality of staple drivers comprises staple drivers of at least two different lengths.

15. The minimally invasive medical fastening device according to claim 13, wherein a longer length of the staple drivers is equal to or greater than a length of a shorter staple driver plus a length of one of the plurality of springs.

16. The minimally invasive medical fastening device according to claim 13, wherein the shutter is a trip wire.

17. The minimally invasive medical fastening device according to claim 13, wherein the shutter is hand-operated from a proximal end of the minimally invasive medical stapling device.

18. The minimally invasive medical fastening device according to claim 13, wherein the shutter is a linear shutter.

19. The minimally invasive medical fastening device according to claim 13, wherein the shutter is a collapsible rotary shutter.

20. The minimally invasive medical fastening device according to claim 13, wherein the staple drivers are movably disposed in the housing.

21. The minimally invasive medical fastening device according to claim 13, wherein the staple drivers sequentially abut the fasteners when the shutter is removed.

* * * * *